US00PP10149P

United States Patent [19]

Twomey

[11] Patent Number: Plant 10,149

[45] Date of Patent: Dec. 16, 1997

[54] HYBRID TEA ROSE PLANT NAMED 'TWOLAD'

[75] Inventor: Jerry Twomey, Leucadia, Calif.

[73] Assignee: DeVor Nurseries, Inc., Watsonville, Calif.

[21] Appl. No.: 414,534

[22] Filed: Mar. 31, 1995

(Under 37 CFR 1.47)

[51] Int. Cl.[6] ..... A01H 5/00

[52] U.S. Cl. ..... Plt./20

[58] Field of Search ..... Plt./20, 19, 17

*Primary Examiner*—Howard J. Locker

*Attorney, Agent, or Firm*—Christie, Parker & Hale, LLP

[57] ABSTRACT

A Hybrid Tea rose variety producing salmon coral flowers.

1 Drawing Sheet

SUMMARY OF THE INVENTION

The present invention relates to a new and distinct Hybrid Tea variety which was originated by my crossing as seed and pollen parents the variety named 'Silver Jubilee' and 'Evening Star' U.S. Plant Pat. No. 3,432, respectively. The varietal denomination of this new rose is 'Twolad'.

Among the novel characteristics possessed by this new variety which distinguish it from its parents and all other varieties of which I am aware are its attractive salmon coral flowers borne on a disease resistant plant.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed.

COMPARISON WITH PARENTS

Whereas the new variety produces salmon coral flowers, the seed parent 'Silver Jubilee' produces pink blend flowers and the pollen parent 'Evening Star' produces medium yellow flowers.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Silver Jubilee'.

*Pollen parent.*—'Evening Star'.

Class: Hybrid Tea.

The following is a detailed description of the new variety, from specimens grown outdoors in Watsonville, Calif. in the mouth of September. The color terminology used is in accordance with The Royal Horticultural Society Colour Chart (RHSCC), and refers to plate numbers in the aforementioned color chart. Phenotypic expression may vary depending on light, environmental and cultural conditions.

Flower

Blooming habit: Recurrent.

A. Bud:

(1) *Size.*—Small.

(2) *Form.*—Pointed and slightly urn shaped, tapering.

(3) *Color.*—When sepals first divide, bud color is near 47A.

(4) *Sepals.*—Longer than bud, about 3 to 4 cm long, foliaceous. Color: Near 144B on top surface, under surface is slightly lighter.

(5) *Peduncle.*—Length: About 6 cm to about 8 cm. Aspect: Small prickles. Strength: Erect, sturdy, slender. Color: Near 144B.

(6) *Bracts.*—One or two; near 147A, leaf shaped, about 5 cm below calyx.

B. Bloom:

(1) *Size.*—Average size when fully expanded — about 8 cm to about 9.5.

(2) *Borne.*—Singly.

(3) *Form.*—Imbricated, i.e., inner petals bend inward in center when about ¾ open to cover flower center, flowers do not fully open readily.

(4) *Petalage.*—Number of petals under normal conditions — about 19 to 23.

(5) *Color (⅓–½ open).*—Outer petals — Top surface: edge of petal near 52A; rest of petal near 52B; base is near 145D; Undersurface: near 52A; base near 145C. Inner petals — Top surface: edge near 52B; rest of petal near 52C; base is near 150D; Undersurface: near 54A; rest of petal 54B; base is near 150D. Base of petals — Apex near 150C. General tonality from a distance — Deep salmon coral.

(6) *Color (Fully open).*—Outer petals — Top surface: edge near 52B; rest of petal 48C; base is 154D; Undersurface: edge between 52A and 52B; rest of petal 52C; base is 145D. Inner petals — Top surface: top edge near 52B; rest of petal near 48B; base is 154D; Undersurface: edge near 52B; rest of petal is 52C; base is 154D. Base of petals — General tonality from a distance — Salmon coral. (7) *Color change.*—This variety is remarkable in how well its color remains constant through blooming. It lightens only to a little lighter shade of salmon-coral. Petal top surface — Changes only slightly in color. Petal undersurface — Changes only slightly in color. Base of petals — Changes only slightly in color. General tonality at a distance — Salmon-coral.

C. Petals:

(1) *Texture.*—Thick, smooth.

(2) *Appearance.*—Inside semi-velvety and outside matte.

(3) *Form.*—Orbicular with some ruffled edges.

(4) *Arrangement.*—Imbricated.

(5) *Petaloids.*—Few.
(6) *Fragrance.*—Mild fruity.
(7) *Lasting quality.*—On plant about 12–15 days, similar in size to pollen parent.
(8) *Persistence.*—Petals drop off cleanly.

Reproductive Organs

A. Stamens:
(1) *Arrangement.*—Regularly arranged around styles.
(2) *Anthers.*—Color near 19A.
(3) *Filaments.*—Near 32A, near 20B at base.
(4) *Pollen.*—Color — near 19A.
B. Pistils:
(1) *Styles.*—Bunched, with even length.
(2) *Stigmas.*—Color near 11B at tip.
C. Characteristics of hips: Not observed.

Plant

A. Form: Upright.
B. Growth: Very vigorous; about 88 cm to about 114 cm in height at first season.
C. Foliage: Compound 3 to 7 leaflets.
(1) *Size.*—Medium, similar in size to pollen parent.
(2) *Quantity.*—Abundant.
(3) *Color.*—New foliage — upper side near 137A underside near 147B; mature foliage — upper side near 147A, underside near 147B.
(4) *Shape.*—Oval.
(5) *Texture.*—Upper side leathery, glossy. Underside semi-leathery, matte.
(6) *Edge.*—Serrated.
(7) *Serration.*—Denticulate.
(8) *Leaf stem.*—Color — medium green.
(9) *Stipules.*—Narrow, bearded with glands, adnate and parallel.
(10) *Rachis.*—Smooth.
(11) *Petioles.*—Top near 174A, underside near 146C.
(12) *Auricle.*—Thin, slightly glandular.
(13) *Resistance to disease.*—Very resistant to blackspot, some mildew and rust.
D. Wood:
(1) *New wood.*—Color near 166B, bark smooth.
(2) *Old wood.*—Color near 146A, bark smooth.
E. Flower stem: About 26 cm to about 41 cm from last cut.
F. Thorns:
*Quantity.*—None on peduncle, present on flowers stems and irregularly spaced.
*Form.*—When present, curved downward.
*Length.*—Medium.
*Color.*—Near 199B with tinge of near 176C at base.
*Position.*—Located in pairs below stipule.
*Prickles.*—Small prickles on peduncle only.
G. Winter hardiness: Winter hardy in Northern and Southern, California.

I claim:

1. A new and distinct Hybrid Tea rose plant variety, substantially as shown and described.

* * * * *

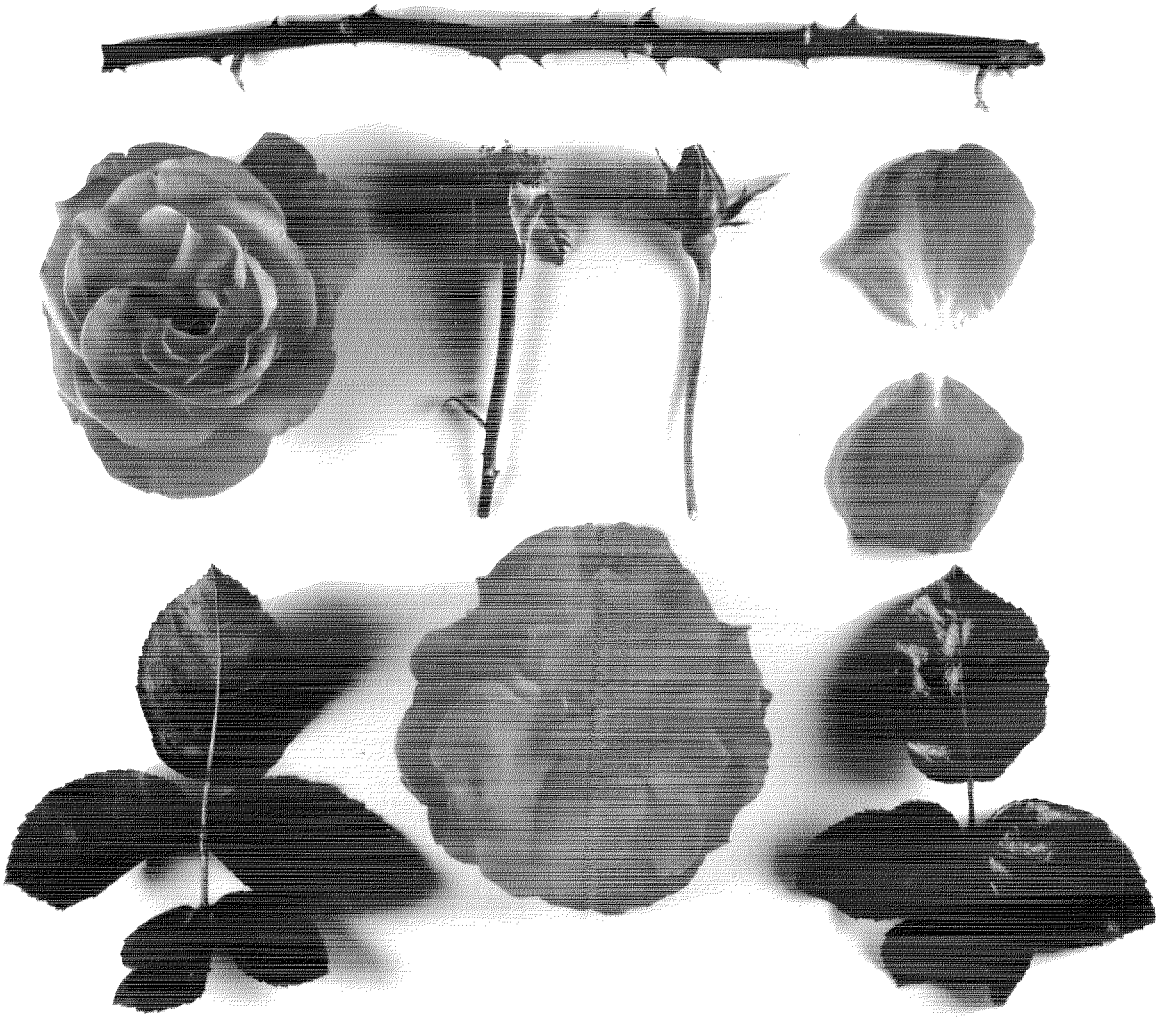

UNITED STATES PATENT AND TRADEMARK OFFICE

CERTIFICATE OF CORRECTION

PATENT NO. : Plant 10,149
DATED : December 16, 1997
INVENTOR(S) : Jerry Twomey

It is certified that error appears in the above-indentified patent and that said Letters Patent is hereby corrected as shown below:

Column 1, line 42, replace "mouth" with -- month --.
Column 2, line 36, replace "Base of petals" with -- Base of petals-150C --.
Column 3, line 3, replace "On plant about 12-15 days, similar in size to pollen parent." with -- On plant about 12-15 days, about 8 to 10 days after cutting. --
Column 4, line 16, replace "flowers" with -- flower --.

Signed and Sealed this

Twenty-second Day of September, 1998

*Attest:*

Bruce Lehman

BRUCE LEHMAN

*Attesting Officer*

*Commissioner of Patents and Trademarks*